US008643709B2

(12) United States Patent
Sato et al.

(10) Patent No.: US 8,643,709 B2
(45) Date of Patent: Feb. 4, 2014

(54) ENDOSCOPE

(75) Inventors: Eijiro Sato, Stamford, CT (US); Eiji Matsuda, Hachioji (JP)

(73) Assignee: Olympus Medical Systems Corp. (JP)

( * ) Notice: Subject to any disclaimer, the term of this patent is extended or adjusted under 35 U.S.C. 154(b) by 790 days.

(21) Appl. No.: 12/472,800

(22) Filed: May 27, 2009

(65) Prior Publication Data

US 2009/0295913 A1 Dec. 3, 2009

(30) Foreign Application Priority Data

May 30, 2008 (JP) ................................. 2008-142891

(51) Int. Cl.
*H04N 7/18* (2006.01)

(52) U.S. Cl.
USPC ................................. 348/65; 348/64; 348/77

(58) Field of Classification Search
None
See application file for complete search history.

(56) References Cited

U.S. PATENT DOCUMENTS

| | | | | |
|---|---|---|---|---|
| 4,867,138 | A * | 9/1989 | Kubota et al. | 348/65 |
| 2004/0249246 | A1 | 12/2004 | Campos | |
| 2007/0177008 | A1 * | 8/2007 | Bayer et al. | 348/65 |
| 2008/0045787 | A1 | 2/2008 | Snay et al. | |

FOREIGN PATENT DOCUMENTS

| | | |
|---|---|---|
| JP | 2003-511140 | 3/2003 |
| JP | 2006-122498 | 5/2006 |
| WO | WO 01/26537 | 4/2001 |

OTHER PUBLICATIONS

Search Report issued by the European Patent Office in connection with corresponding No. EP 09 007 152.3 on Sep. 1, 2009.

Letter from German associate dated Sep. 2, 2009 forwarding the European Search.

Report dated Sep. 1, 2009 to Japanese associate, including discussion of relevancy thereof.

Office Action issued by the Japanese Patent Office on Oct. 23, 2012 in connection with corresponding Japanese Patent Application No. 2008-142891.

Translation of Office Action issued by the Japanese Patent Office on Oct. 23, 2012 in connection with corresponding Japanese Patent Application No. 2008-142891.

* cited by examiner

*Primary Examiner* — Thu Nguyen
*Assistant Examiner* — Nam Tran
(74) *Attorney, Agent, or Firm* — Ostrolenk Faber LLP

(57) ABSTRACT

An endoscope includes an image pick-up unit extending in the axial direction within a distal end forming portion, and a channel tube extending in the axial direction within the distal end forming portion and including a parallel portion arranged parallel with the image pick-up unit, and the outer peripheral surface of the parallel portion includes a facing side diameter reducing portion arranged on a side facing the image pick-up unit and, with respect to a reference circumferential surface including a common central axis to the inner peripheral surface of the parallel portion, closer to a central axis side than the reference circumferential surface in a cross section orthogonal to the axial direction, and a diameter keeping portion arranged on a side other than the side facing the image pick-up unit and whose at least a part overlaps the reference circumferential surface.

4 Claims, 9 Drawing Sheets

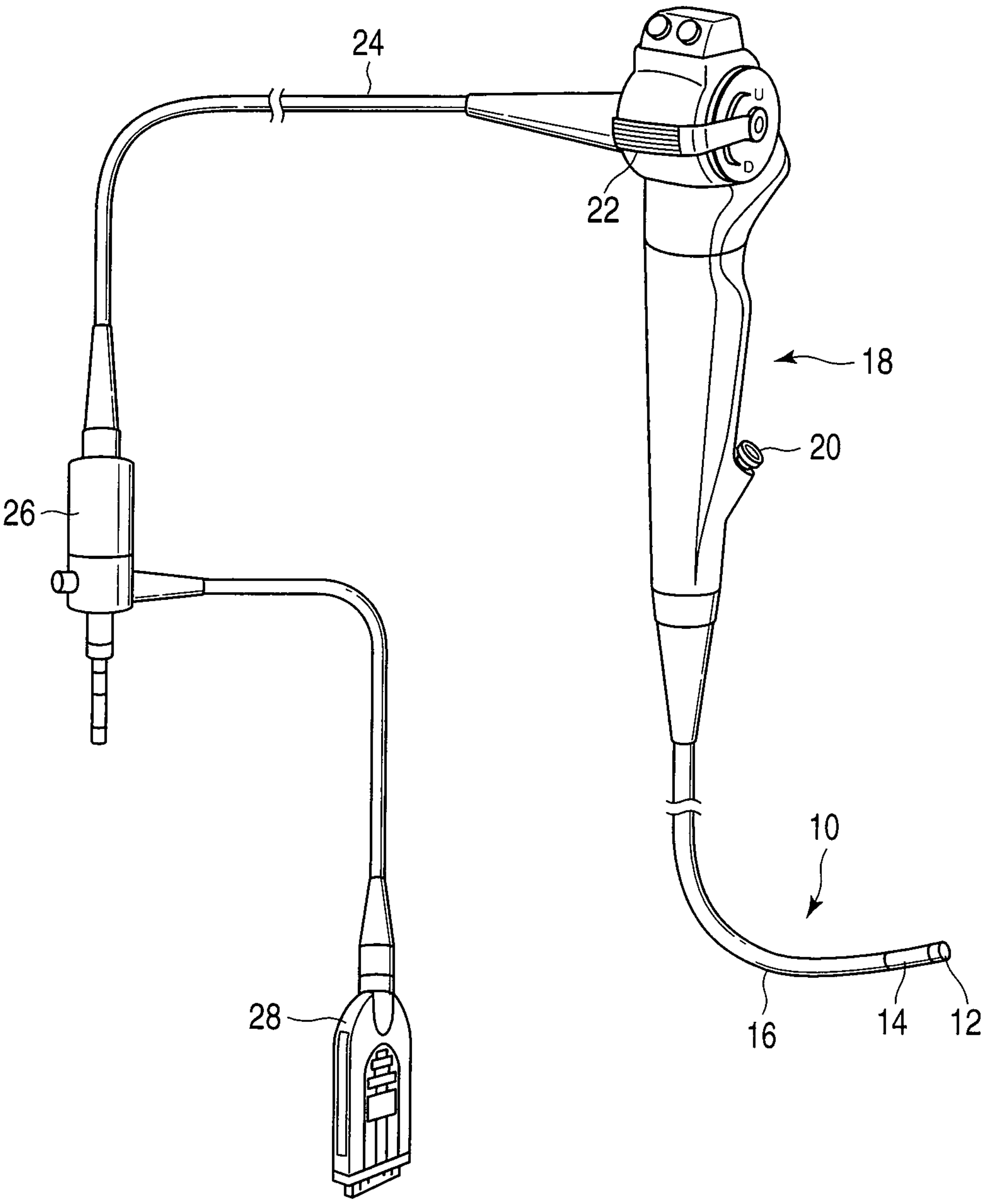
F I G. 1

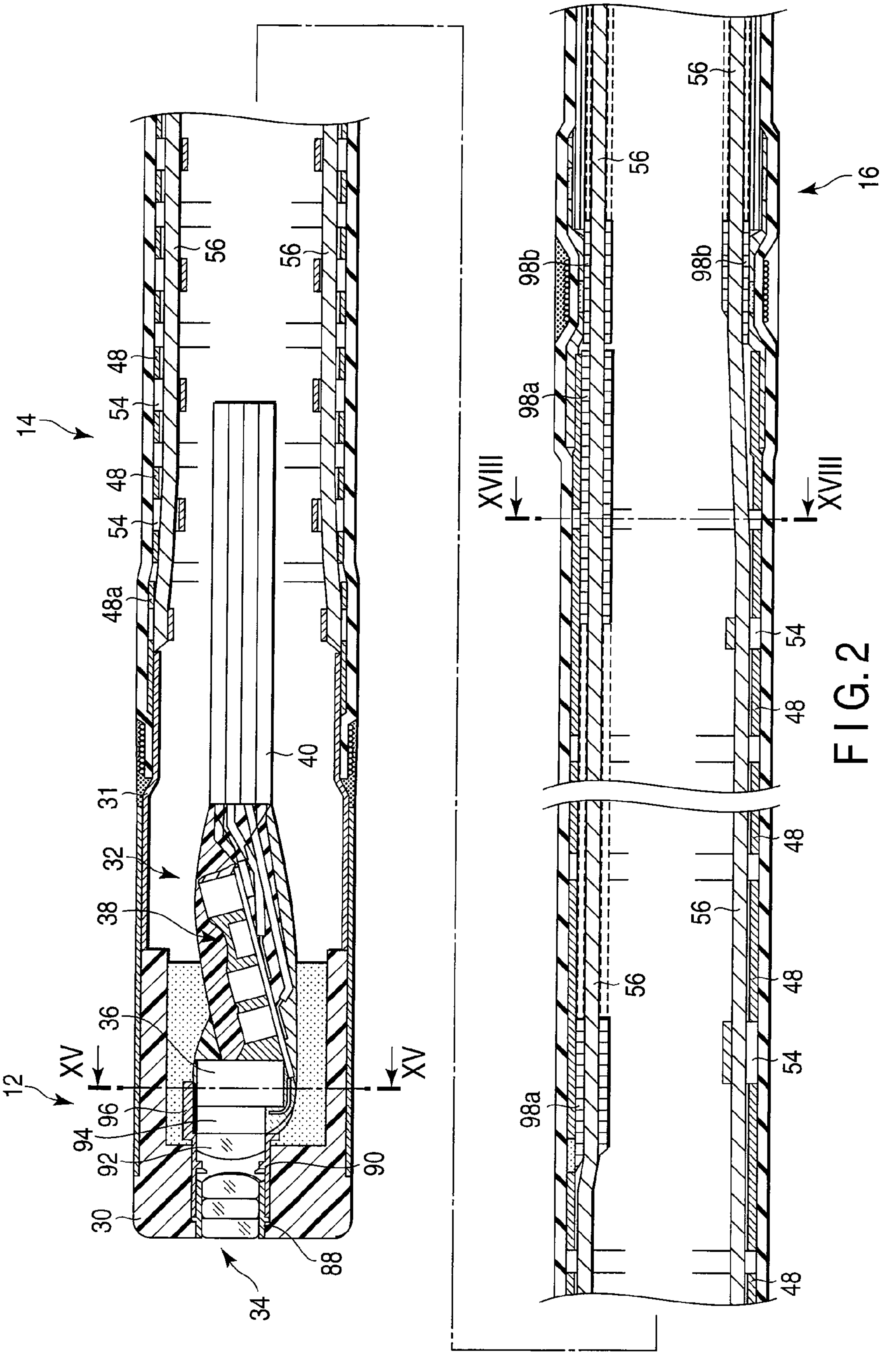
F I G. 2

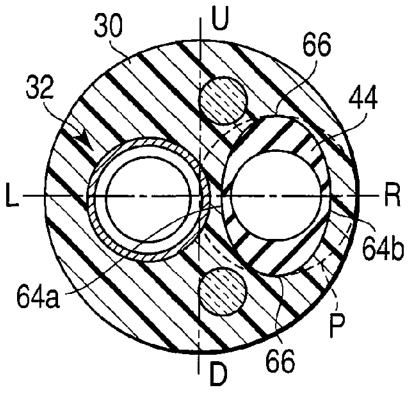
F I G. 7
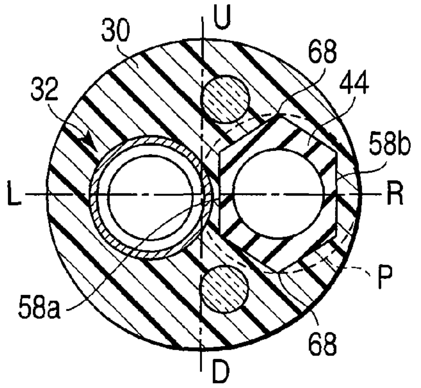
F I G. 8
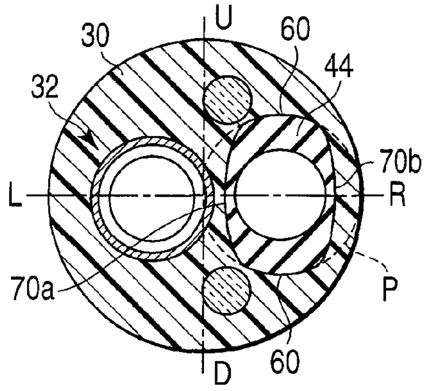
F I G. 9

ENDOSCOPE

CROSS-REFERENCE TO RELATED APPLICATIONS

This application is based upon and claims the benefit of priority from the prior Japanese Patent Application No. 2008-142891, filed May 30, 2008, the entire contents of which are incorporated herein by reference.

BACKGROUND OF THE INVENTION

1. Field of the Invention

The present invention relates to an endoscope wherein an image pick-up unit and a channel tube are built in a distal end forming portion.

2. Description of the Related Art

An endoscope includes an elongate insertion portion configured to be inserted into a cavity. A channel tube through which an accessory is to be inserted extends within the insertion portion. The distal end portion of the channel tube is arranged within a distal end rigid portion as a distal end forming portion on the distal end portion of the insertion portion. Moreover, an image pick-up unit configured to pick up an observation image is built in the distal end rigid portion. The channel tube and the image pick-up unit are arranged parallel with each other and extend in the axial direction in the distal end rigid portion.

In Jpn. Pat. Appln. KOHYO Publication No. 2003-511140, it is disclosed that the inner peripheral surface of a channel tube is formed into various shapes in the cross section orthogonal to the axial direction in order to improve an operability in moving forward and backward an accessory in the channel tube and secure a sufficient fluid flow.

BRIEF SUMMARY OF THE INVENTION

In an aspect of the present invention, an endoscope includes: a distal end forming portion forming a distal end portion of the endoscope and extending in an axial direction; an image pick-up unit extending in the axial direction within the distal end forming portion; and a channel tube extending in the axial direction within the distal end forming portion and including a parallel portion arranged parallel with the image pick-up unit, and the parallel portion includes an inner peripheral surface and an outer peripheral surface, and the outer peripheral surface includes: a facing side diameter reducing portion arranged on a side facing the image pick-up unit and, with respect to a reference circumferential surface including a common central axis to the inner peripheral surface, closer to a central axis side than the reference circumferential surface in a cross section orthogonal to the axial direction; and the diameter keeping portion arranged on a side other than the side facing the image pick-up unit and whose at least a part overlaps the reference circumferential surface.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view showing an endoscope according to an embodiment of the present invention;

FIG. 2 is a longitudinal cross sectional view showing an insertion portion according to the embodiment of the present invention;

FIG. 7 is a transverse cross sectional view showing a distal end rigid portion according to a third variation example of the embodiment of the present invention;

FIG. 8 is a transverse cross sectional view showing a distal end rigid portion according to a fourth variation example of the embodiment of the present invention;

FIG. 9 is a transverse cross sectional view showing a distal end rigid portion according to a fifth variation example of the embodiment of the present invention;

DETAILED DESCRIPTION OF THE INVENTION

Figure 3:
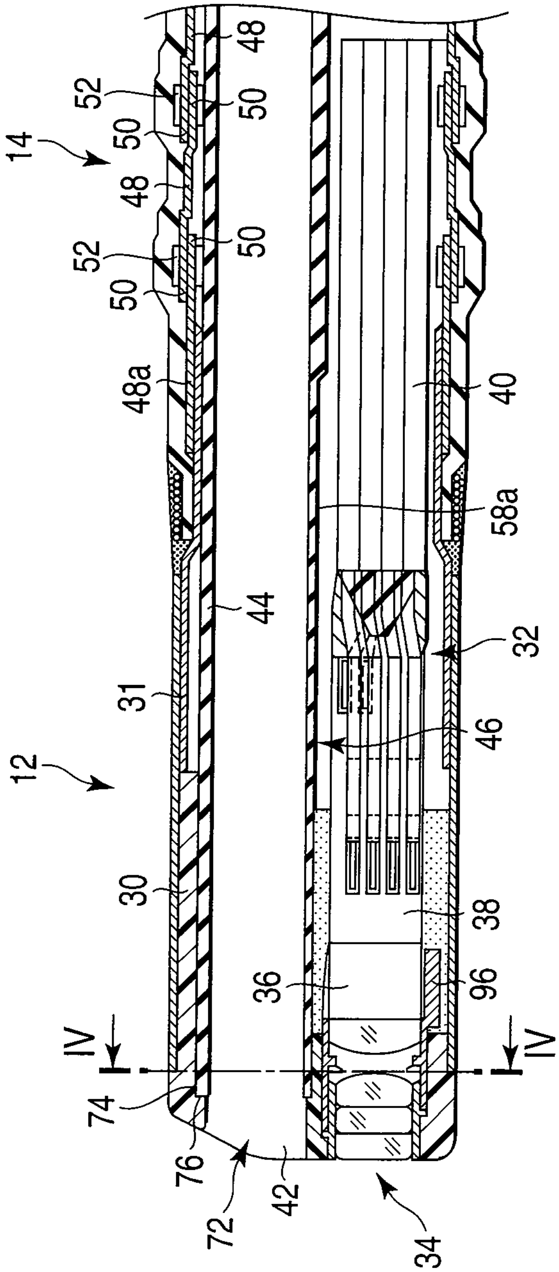
FIG. 3 is another longitudinal cross sectional view showing the insertion portion according to the embodiment of the present invention.

Hereinafter, an embodiment of the present invention will be explained referring to the drawings.

Referring to FIG. 1, a schematic structure of an endoscope will be explained.

The endoscope includes an elongate insertion portion 10 configured to be inserted into a cavity in the body. In the insertion portion 10, a distal end rigid portion 12 as a distal end forming portion, a bending portion 14 operated to be bent and a long and flexible insertion tube portion 16 is provided from the distal end side to the proximal end side. The proximal end portion of the insertion portion 10 is connected to an operation portion 18 configured to be held and operated by an operator. The operation portion 18 is provided with an accessory inserting opening 20 into which an accessory is to be inserted and a bending operation lever 22 configured to operate the bending portion 14 to be bent. A universal cable 24 extends from the operation portion 18, and the proximal end portion of the universal cable 24 is provided with a light source connecter 26 and an electric connecter 28 configured to be connected to a light source apparatus and a video processor, respectively.

Referring to FIGS. 1 to 3, a schematic structure of the insertion portion 10 will be explained.

In the distal end rigid portion 12, a distal end member 30 and a connecting member 31 is provided from the distal end side to the proximal end side. An image pick-up unit 32 configured to pick up an observation image is built in the distal end rigid portion 12. In the image pick-up unit 32, a group of objective lens 34, an image pick-up device 36 and an electronic substrate 38 on which electronic devices are mounted are provided from the distal end side to the proximal end side, and the image pick-up unit 32 extends in the axial direction. Various kinds of signal line extend from the electronic substrate 38 of the image pick-up unit 32, and the various kinds of signal line are gathered into an image pick-up cable 40. The image pick-up cable 40 is inserted through the endoscope to be connected to the electric connecter 28. On the other hand, an accessory protruding opening 42 is formed on the distal end rigid portion 12 through which the accessory is to be protruded. The distal end of a channel tube 44 through which the accessory is to be inserted is connected to the inner end portion of the accessory protruding opening 42. The channel tube 44 extends in the axial direction and is arranged parallel with the image pick-up unit 32 and the distal end portion of the image pick-up cable 40 to form a parallel portion 46 in the distal end rigid portion 12. Furthermore, the channel tube 44 is inserted through the insertion portion 10, put into the operation portion 18, and then connected to the inner end portion of the accessory inserting opening 20 in the operation portion 18.

In the bending portion 14, a large number of bending parts 48 having substantially circularly cylindrical shapes are coupled in order coaxially with each other so as to be rotatable with respect to each other. That is, in the bending part 48, a pair of tongue portions 50 protrudes from both the end surfaces of a circularly cylindrical portion symmetrically with each other with respect to the central axis, respectively, and both the tongue portions 50 of the both bending parts 48 adjoining with each other are overlapped with each other and coupled so as to be rotatable with respect to each other by a rivet 52 orthogonal to the axial direction. Both the pairs of the tongue portions 50 on both the end surfaces are arranged at the same position as each other with respect to the peripheral direction in each of the bending parts 48, rotational directions in the pairs of the bending parts 48 adjoining with each other are equal to each other, and the bending portion 14 can be operated to be bent in only two orientations. The two orientations are referred as an up and down direction and direction which is left and right with respect to the up and down direction when viewed from the proximal end side is referred as a left and right direction. In the drawings, up, down, left and right is shown as U, D, L and R. Wire insertion portions 54 are formed at the up and the down position on the inner peripheral surface of the circularly cylindrical portion of the bending part 48. Operation wires 56 are inserted through the wire insertion portions 54 so as to movable forward and backward. The distal end portion of the operation wire 56 is fixed to a distal end bending part 48*a*. It is noted that the pair of the tongue portions 50 is not formed on the distal end side in the distal end bending part 48*a*, the proximal end portion of the connecting member 31 of the distal end rigid portion 12 is fitted into from the distal end side and fixed to the distal end bending part 48*a*. The operation wire 56 is inserted through the insertion portion 10, put into the operation portion 18, and connected to a bending mechanism within the operation portion 18. When the bending operation lever 22 is operated, the bending mechanism move backward and forward or move forward and backward the up and the down operation wire 56 and the bending portion 14 is operated to be bent in the up orientation or the down orientation.

Figure 4:
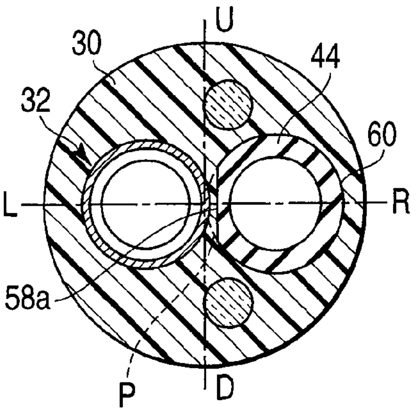
FIG. 4 is a transverse cross sectional view showing a distal end rigid portion according to the embodiment of the present invention cutting along the IV-IV line in FIG. 3.
Figure 5:
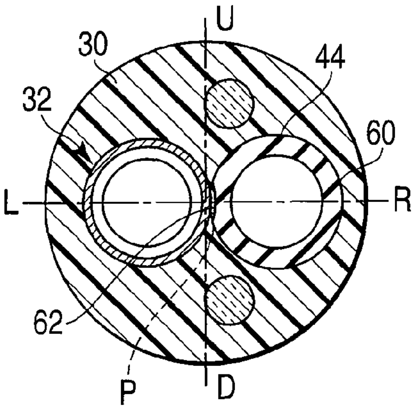
FIG. 5 is a transverse cross sectional view showing a distal end rigid portion according to a first variation example of the embodiment of the present invention.

Referring to FIGS. 3 to 5, a structure for making the diameter of the distal end rigid portion 12 thinner will be explained.

The image pick-up unit 32 and the channel tube 44 are arranged side by side in the left and right direction, and the image pick-up unit 32 is arranged on the left side and the channel tube 44 is arranged on the right side. Although the channel tube 44 has a substantially circularly cylindrical shape, a so-called D-cut is formed on the left side facing the image pick-up unit 32 in the cross section orthogonal to the axial direction in the parallel portion 46 within the distal end rigid portion 12. In the channel tube 44, the thickness is reduced on the left side facing the image pick-up unit 32 and kept on the up and the down side which are bending directional sides. The D-cut shape extends over the whole parallel portion 46 in the axial direction.

In other words, the inner peripheral surface of the parallel portion 46 of the channel tube 44 forms a circumferential surface. The outer peripheral surface of the parallel portion 46 includes a facing side plane surface 58*a* as a facing side diameter reducing portion arranged on the left side facing the image pick-up unit 32 and closer to a central axis side than a reference circumferential surface P including the common central axis to the inner peripheral surface in the cross section orthogonal to the axial direction. Moreover, the outer peripheral surface of the parallel portion 46 includes a circular arc peripheral surface 60 as the diameter keeping portion arranged on the up, the right and the down side other than the left side facing the image pick-up unit 32 and the whole circular arc peripheral surface overlaps the reference circumferential surface P. In the channel tube 44, the thickness is reduced between the inner peripheral surface and the facing side plane surface 58*a* on the left side facing the image pick-up unit 32, while the thickness is kept between the inner peripheral surface and the circular arc peripheral surface 60 on the up and the down side which are bending directional sides. The facing side plane surface 58*a* and the circular arc peripheral surface 60 extend over the whole parallel portion 46 in the axial direction.

In the present embodiment, in the outer peripheral surface of the parallel portion 46 of the channel tube 44, the D-cut shape, in other words, the facing side plane surface 58*a* arranged closer to the central axis side than the reference circumferential surface P is formed on the left side facing the image pick-up unit 32, and therefore, it is possible to arrange the central axes of the channel tube 44 and the image pick-up unit 32 close to each other, whereby enabling to make the diameter of the distal end rigid portion 12 thinner. Here, in the case where the diameter of the distal end rigid portion 12 is made thinner by reducing the outer diameters themselves of the channel tube 44 and the image pick-up unit 32, deterioration in durability and performance is brought about due to deterioration in an insertion capability for the accessory by a diminution in the inner diameter of the channel tube 44, deterioration in durability by a diminution in thickness of the channel tube 44, a decrease in the number of pixels by reduction in the objective lens and in the image pick-up unit 32, and so on. In contrast, in the present embodiment, it is possible to make the diameter of the distal end rigid portion 12 thinner without bringing about deterioration in durability and performance.

Moreover, a minimum protruding length of the accessory wherein the accessory become be able to be observed by the image pick-up unit 32 when protruding the accessory from the accessory protruding opening 42 is referred as an accessory minimum visible distance. As is mentioned above, it is possible to arrange the central axes of the channel tube 44 and the image pick-up unit 32 close to each other, and therefore, it is possible to the central axes of the accessory protruding opening 42 and a field of view of the image pick-up unit 32 close to each other, whereby enabling to reduce the accessory minimum visible distance to improve a treatment ability.

Furthermore, in the case where the accessory is moved forward and backward in the state where the bending portion 14 is bent, the accessory is moved forward and backward along the inner peripheral surface opposite to a bending orientation of the channel tube 44, and therefore, parts on the bending directional sides are worn by the accessory in the channel tube 44. In the outer peripheral surface of the channel tube 44, the D-cut shape is not formed, in other words, the circular arc peripheral surface 60 wherein the whole circular arc peripheral surface 60 overlaps the reference circumferential surface P is formed, on the up and the down side which are the bending directional sides, and therefore, the thickness of the channel tube 44 is kept on the up and the down side which are the bending directional sides, whereby keeping durability of the channel tube 44.

Referring to FIGS. 5 to 9, channel tubes 44 according to a first to a fifth variation examples will be explained.

Referring to FIG. 5, in a parallel portion 46 of a channel tube 44 according to the first variation example, a concave curved peripheral surface 62 depressed toward the central axis is formed on the left side facing an image pick-up unit 32 in stead of the facing side plane surface 58*a* according to the first embodiment.

Figure 6:
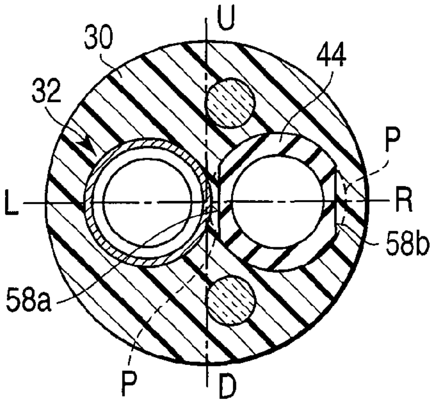
FIG. 6 is a transverse cross sectional view showing a distal end rigid portion according to a second variation example of the embodiment of the present invention.

Referring to FIG. 6, in a parallel portion 46 of a channel tube 44 according to the second variation example, a D-cut shape is formed on the right side opposite to the left side facing an image pick-up unit 32 in the cross section orthogonal to the axial direction. In other words, the outer peripheral surface of the parallel portion 46 includes an opposite side plane surface 58*b* as an opposite side diameter reducing portion arranged on the right side opposite to the left side facing the image pick-up unit 32 and closer to a central axis side than a reference circumferential surface P in the cross section orthogonal to the axial direction. Therefore, it is possible to make the diameter of a distal end rigid portion 12 thinner. Moreover, the thickness is still kept on the up and the down side which are bending direction sides in the channel tube 44, whereby keeping durability of the channel tube 44.

Referring to FIG. 7, in a parallel portion 46 of a channel tube 44 according to the third variation example, the outer peripheral surface forms an elliptic peripheral surface whose major axial direction corresponds to a bending direction in the cross section orthogonal to the axial direction. In other words, curved peripheral surfaces with small curvature on the left side facing an image pick-up unit 32 and the right side opposite to the left side, that is, the left side and the right side which are end portion sides in a minor axial direction of the elliptic peripheral surface forms a facing side convex curved peripheral surface 64*a* and a opposite side convex curved peripheral surface 64*b* as a facing side diameter reducing portion and an opposite side diameter reducing portion arranged closer to central axis sides than a reference circumferential surface P, respectively. Moreover, curved peripheral surfaces with large curvature on the up and the down side which are bending directional sides, that is, the up and the down side which are end portion sides in the major axial direction of the elliptic peripheral surface forms convex curved peripheral surfaces 66 as diameter keeping portions whose end portions overlap a reference circumferential surface P.

Referring to FIG. 8, in a parallel portion 46 of a channel tube 44 of the fourth variation example, the outer peripheral surface forms a hexagon including a symmetrical axis passing two apexes thereof and being longer in a symmetrical axial direction, and the symmetrical axial direction corresponds to a bending direction in the cross section orthogonal to the axial direction. In other words, a facing side plane surface 58*a* and an opposite side plane surface 58*b* as a facing side diameter reducing portion and an opposite side diameter reducing portion arranged closer to central axis sides than a reference circumferential surface P is formed on the left side facing an image pick-up unit 32 and the right side opposite to the left side, respectively. Moreover, convex peripheral surfaces 68 as diameter keeping portions whose apex portions overlap a reference circumferential surface P are formed on the up and the down side which are bending directional sides.

Referring to FIG. 9, in a parallel portion 46 of a channel tube 44 according to the fifth variation example, a facing side elliptic arc peripheral surface 70*a* and an opposite side elliptic arc peripheral surface 70*b* as a facing side diameter reducing portion and an opposite side diameter reducing portion arranged closer to central axis sides than a reference circumferential surface P are formed on the left side facing an image pick-up unit 32 and the right side opposite to the left side in the outer peripheral surface in the cross section orthogonal to the axial direction, and the facing side elliptic arc peripheral surface 70*a* and the opposite side elliptic arc peripheral surface 70*b* forms parts of the elliptic peripheral surface whose major axial direction corresponds to a bending direction. Moreover, circular arc peripheral surfaces 60 as a diameter keeping portion wherein the whole circular arc peripheral surfaces 60 overlap a reference circumferential surface P are formed on the up and the down side which are bending directional sides.

Figure 10:
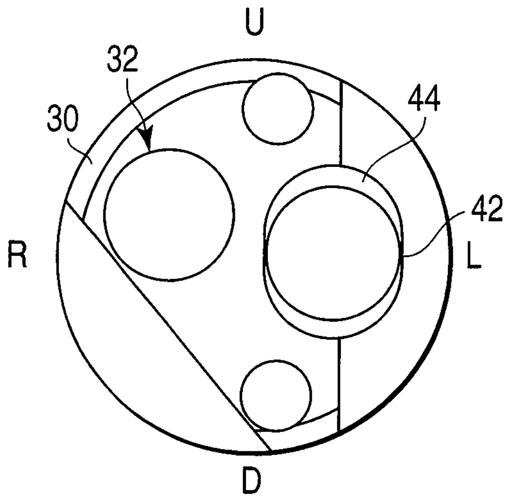
FIG. 10 is a front view showing the distal end rigid portion according to the embodiment of the present invention.
Figure 11:
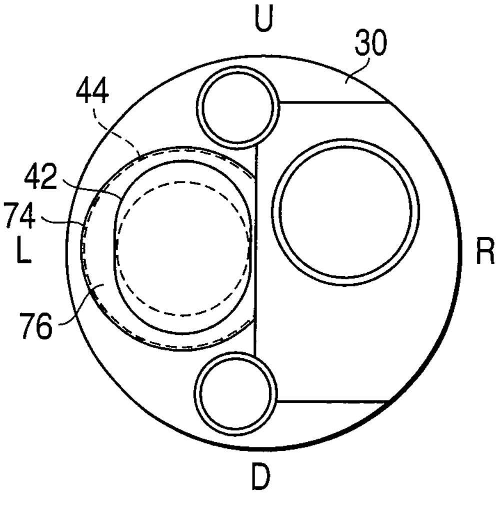
FIG. 11 is a back view showing a distal end member according to the embodiment of the present invention.

Referring to FIGS. 3, 10 and 11, a structure for coupling the distal end member 30 and the channel tube 44 to each other will be explained.

A channel bore 72 is formed in the axial direction through the distal end member 30. The proximal end side of the channel bore 72 forms a fixing opening 74 whose inner diameter is substantially equal to the outer diameter of the channel tube 44 and the distal end side of the channel bore 72 forms the accessory protruding opening 42 whose diameter is thinner than that of the fixing opening 74. A step portion between the fixing opening 74 and the accessory protruding opening 42 forms an abutment portion 76. The channel tube 44 is fitted into the fixing opening 74, abutted against the abutment portion 76, and fixed to the distal end member 30.

Here, in the case where the inner peripheral surface of the accessory protruding opening 42 is arranged to be inner than the inner peripheral surface of the channel tube 44 in the cross section orthogonal to the axial direction, the accessory may be caught by the distal end member 30 when protruding and retracting the accessory through the accessory protruding opening 42. In order to prevent such catching, it is necessary to arrange the inner peripheral surface of the accessory protruding opening 42 to be outer than the inner peripheral surface of the channel tube 44. In particular, the accessory is moved forward and backward along the inner surface on the side opposite to a bending orientation in the state where the bending portion 14 is bent, and therefore, it is necessary to securely arrange the inner peripheral surface of the accessory protruding opening 42 to be outer than the inner peripheral surface of the channel tube 44 regarding the bending directional sides. On the other hand, in the case where the inner diameter of the accessory protruding opening 42 is increased, the abutment part between the distal end member 30 and the channel tube 44 is decreased, a clearance is generated between the distal end member 30 and the channel tube 44, whereby hindering secure abutting and fixing.

In the present embodiment, the cross sectional shape of the accessory protruding opening 42 forms an elliptic shape whose major axial direction is the bending direction, the length of the major axis is sufficiently larger than the inner diameter of the channel tube 44, and the length of the minor axis is slightly smaller than the inner diameter of the channel tube 44. Therefore, the inner peripheral surface of the accessory protruding opening 42 is securely arranged to be outer than the inner peripheral surface of the channel tube 44 in the end portion sides in the major axial direction which are bending direction sides, and also, the abutment part between the distal end member 30 and the channel tube 44 is sufficiently secured on the end portion sides in a minor axial direction.

As is mentioned above, in the present embodiment, the cross sectional shape of the accessory protruding opening 42 is longer in the bending direction, and therefore, it is possible to prevent the distal end member 30 and the accessory from being caught by each other, and also securely abut and fix the distal end member 30 and the channel tube 44 against and to each other without a clearance.

It is noted that an accessory protruding opening 42 has a shape of a cross extending an up and down direction and an left and right direction in the case where the bending portion 14 is configured to be operated to be bent in four orientations, that is, an up, a down, a left and a right direction.

Figure 12:
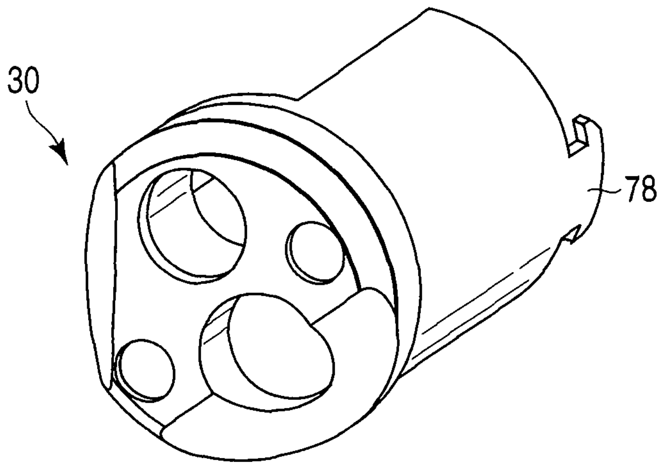
FIG. 12 is a perspective view showing the distal end member according to the embodiment of the present invention.
Figure 13:
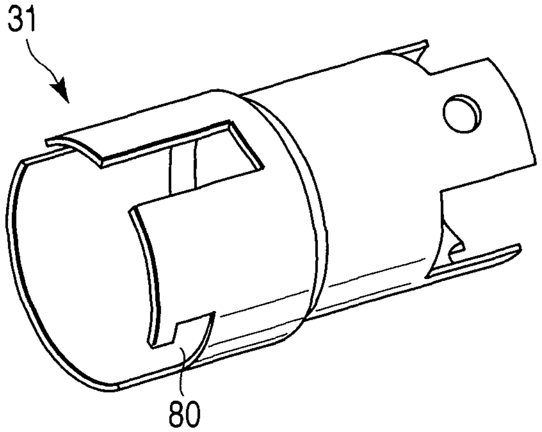
FIG. 13 is a perspective view showing a connecting member according to the embodiment of the present invention.

Referring to FIGS. 2, 12 and 13, a structure for coupling the distal end member 30 and the connecting member 31 in the distal end rigid portion 12 to each other will be explained.

The distal end surface of the distal end member 30 and the distal end surface of the connecting member 31 are abutted against, and bonded to be fixed to each other. In such bonding fixing through abutting, when the distal end member 30 and the connecting member 31 are positioned with respect to each other, there is not what functions an indicator in the positioning, in particular, with respect to a rotational direction about the central axis, and therefore, there is a possibility that the distal end member 30 and the connecting member 31 are assembled in an erroneous positional relationship. In the present embodiment, a fitting portion 78 protrudes from the proximal end surface of the distal end member 30 toward the proximal end side. The fitting portion 78 includes a finger portion extending in the axial direction and a pair of claw portions protruding from the terminal end of the finger portion toward both the sides in the peripheral direction, and has a substantially T-shape. On the other hand, a fitting receiving portion 80 having a shape corresponding to the fitting portion 78 is formed in the distal end portion of the connecting member 31. The fitting portion 78 of the distal end member 30 is fitted into the fitting receiving portion 80 of the connecting member 31, and the distal end member 30 and the connecting member 31 are positioned with respect to each other. As is mentioned above, in the present embodiment, it is possible to correctly position the distal end member 30 and the connecting member 31 with respect to each other and also it is possible to securely assemble the distal end member 30 and the connecting member 31 in the correct positional relationship, without making the diameter of the distal end rigid portion 12 thicker.

Figure 14:
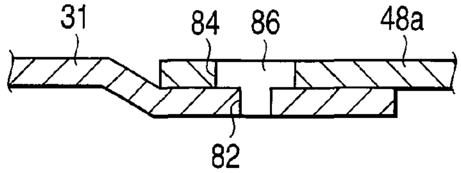
FIG. 14 is an enlarge cross sectional view showing the connecting member and a distal end bending part according to the embodiment of the present invention.

Referring to FIGS. 2 and 14, a structure for coupling the connecting member 31 of the distal end rigid portion 12 and the distal end bending part 48*a* of the bending portion 14 to each other will be explained.

A proximal end side thin circularly cylindrical portion of the connecting member 31 is fitted on and bonded to be fixed to a distal end side thin circularly cylindrical portion of the distal end bending part 48*a* from the distal end side. In this case, as is similar to the case of the distal end member 30 and the connecting member 31, when the connecting member 31 and the distal end bending part 48*a* are positioned with respect to each other, there is not what functions as an indicator in the positioning, in particular, with respect to the rotational direction about the central axis, there is a possibility that the connecting member 31 and the distal end bending part 48*a* are assembled in an erroneous positional relationship. In the present embodiment, an inside coupling bore 82 whose cross section is circular is formed radially through the proximal end side thin circularly cylindrical portion of the connecting member 31. On the other hand, an outside coupling bore 84 whose cross section is circular is formed radially through the distal end side thin circularly cylindrical portion of the distal end bending part 48*a*. The inner diameter of the outside coupling bore 84 is larger than the inner diameter of the inside coupling bore 82, and the inside coupling bore 82 and the outside coupling bore 84 are arranged coaxially with each other. A stepped pin 86 or a screw is fitted into the inside coupling bore 82 and the outside coupling bore 84, and the connecting member 31 and the distal end bending part 48*a* are positioned with respect to each other, and also, fixing strength between both the members is increased. As is mentioned above, in the present embodiment, it is possible to correctly position the connecting member 31 and the distal end bending part 48*a* with respect to each other, and therefore, it is possible to securely assemble the connecting member 31 and the distal end bending part 48*a* in the correct positional relationship, and also, it is possible to increase fixing strength between the connecting member 31 and the distal end bending part 48*a*, without making the diameter of the distal end portion of the bending portion 14 thicker and making an assembly for the connecting member 31 and the distal end bending part 48*a* complicated.

Figure 15:
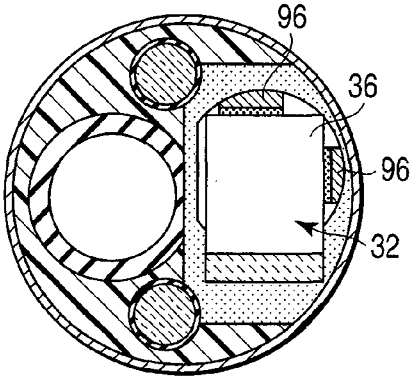
FIG. 15 is a transverse cross sectional view showing the distal end rigid portion according to the embodiment of the present invention cutting along the XV-XV line in FIG. 2.
Figure 16:
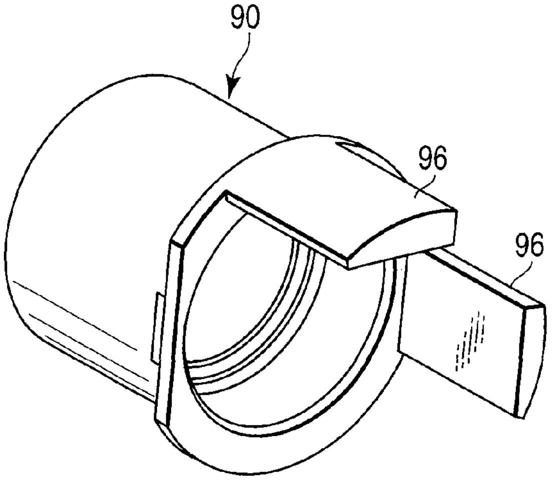
FIG. 16 is a perspective view showing a lens frame according to the embodiment of the present invention.

Referring to FIGS. 2, 15 and 16, a structure for joining optical members to each other in the image pick-up unit 32 will be explained.

In the image pick-up unit 32, a circularly cylindrical distal end side lens frame 88 and a circularly cylindrical proximal end side lens frame 90 are coaxially coupled to each other from the distal end side to the proximal end side. Objective lenses are inserted into and fixed to the distal end side lens frame 88 and arranged side by side in the axial direction. The proximal end objective lens 92 is inserted into and fixed to the proximal end portion of the proximal end side lens frame 90. Furthermore, the proximal end objective lens 92, the cover glass 94, and the image pick-up device 36 are arranged side by side from the distal end side to the proximal end side, and the proximal end surface of the proximal end objective lens 92 and the distal end surface of the cover glass 94 are bonded to be fixed to each other. Bounding strength is low in the bounding place, and therefore, there is a possibility that bounding position is shifted due to an impact in assembling or using to make it impossible to obtain a good image. In the present embodiment, extending portions 96 having shapes of a plate extends from the proximal end surface of the proximal end side lens frame 90. The inner surface of each extending portion 96 is arranged over the side surface of the image pick-up device 36, and bonded to be fixed to the side surface of the image pick-up device 36. Moreover, each extending portion 96 is arranged in an empty space within the distal end rigid portion 12. As is mentioned above, in the present embodiment, it is possible to prevent the bonding position between the proximal end objective lens 92 and the cover glass 94 from being shifted and always obtain a good image, without making the diameter of the distal end rigid portion 12 thicker.

Figure 17:
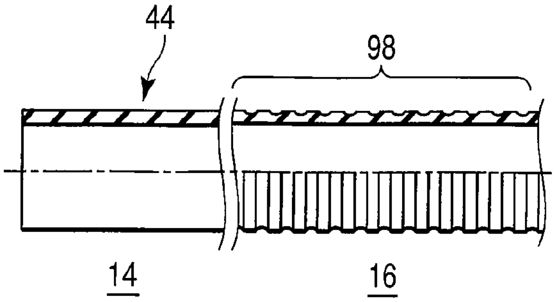
FIG. 17 is a longitudinal cross sectional and side view showing a channel tube according to the embodiment of the present invention.

Referring to FIGS. 2 and 17, a structure of the channel tube 44 in the bending portion 14 and the insertion tube portion 16 will be explained.

The channel tube 44 is inserted through the bending portion 14 and the insertion tube portion 16. Here, a bending angle in the bending portion 14 is limited within a certain range, and therefore, in the bending portion 14, the channel tube 44 is not bent to so large extent and there is a low possibility that the channel tube 44 is buckled. On the other hand, a bending angle in the insertion tube portion 16 is not limited and the insertion tube portion 16 may be bent to a large extent due to an application of an external force, and therefore, there is a possibility that the channel tube 44 is bent to a large extent to be buckled. In the present embodiment, an only part 98 of the outer peripheral surface of the channel tube 44, which is arranged in the insertion tube portion 16, is processed through a so-called wrinkling process and a helical winding groove is closely formed in the part 98, whereby increasing buckling strength of the channel tube 44.

Figure 18:
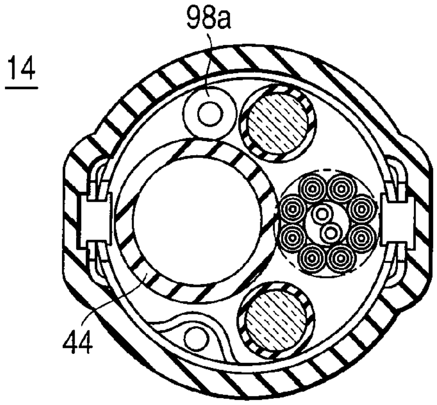
FIG. 18 is a transverse cross sectional view showing a bending portion according to the embodiment of the present invention cutting along the XVIII-XVIII line in FIG. 2.
Figure 19:
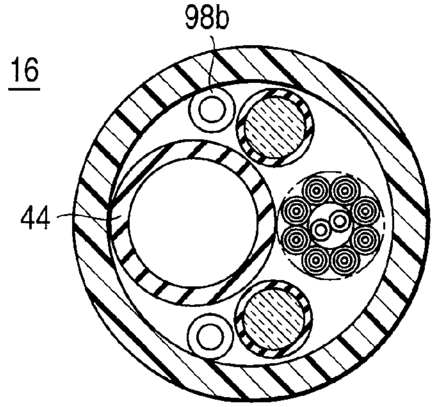
FIG. 19 is a transverse cross sectional view showing an insertion tube portion according to the embodiment of the present invention.

Referring to FIGS. 2, 18 and 19, a structure of coil sheaths in the bending portion 14 and the insertion tube portion 16 will be explained.

Regarding the bending portion 14, the wire insertion portions 54 are formed at the up and the down position in each of a certain number of bending parts 48 on the distal end side and the wire insertion portion 54 is formed in the only down position in each of the other bending parts 48 on the proximal end side. In the other bending parts 48 on the proximal end side, a distal end side coil sheath 98*a* extends in the axial direction at the up position. The only distal end portion of the distal end side coil sheath 98*a* is fixed to the inner peripheral surface of the bending part 48. On the other hand, in the insertion tube portion 16, proximal end side coil sheaths 98*b* are arranged at the up and the down position. The distal end portion of the proximal end side coil sheath 98*b* is fixed to the inner peripheral surface of the distal end portion of the insertion tube portion 16. The proximal end surface of the distal end side coil sheath 98*a* on the up position is arranged to face the distal end surface of the proximal end side coil sheath 98*b* at the up position. The operation wire 56 at the up position is inserted through the wire insertion bore, the distal end side coil sheath 98*a*, and the proximal end side coil sheath 98*b*, and the operation wire 56 at the down position is inserted through the wire insertion bore, and the proximal end side coil sheath 98*b*. When the bending portion 14 is bent in the down orientation, the operation wire 56 at the down position is moved backward, and the whole bending portion 14 is bent in the down orientation. On the other hand, when the bending portion 14 is bent in the up orientation, the operation wire 56 at the up position is moved backward, and the distal end side coil sheath 98*a* at the up position is moved toward the proximal end side, the proximal end surface of the distal end side coil sheath 98*a* at the up position and the distal end surface of the proximal end side coil sheath 98*b* at the up position are abutted against each other, and the distal end side coil sheath 98*a* functions as a tension rod, an only part in which the distal end side coil sheath 98*a* is not arranged is bent in the bending portion 14. That is, bent shapes of the bending portion 14 in the cases of bending in the down orientation and bending in the up orientation are different from each other, and the distal end side coil sheath 98*a* functions to control the bent shapes.

Here, when the bending portion 14 is operated to be bent, in the case where the distal end side coil sheath 98*a* is put into a clearance between the other built-in members, there is a possibility that the bending portion 14 does not become a desired bent shape. In the present embodiment, the outer diameter of the distal end side coil sheath 98*a* is larger than that of the outer diameter of the proximal end side coil sheath 98*b*. Therefore, when the bending portion 14 is operated to be bent, the distal end side coil sheath 98*a* is prevented from being put into the clearance between the other built-in members, and therefore, it is possible to securely obtain the desired bent shape.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:

a distal end forming portion forming a distal end portion of the endoscope and extending in an axial direction;

an image pick-up unit extending in the axial direction within the distal end forming portion; and a channel tube extending in the axial direction within the distal end forming portion and including a parallel portion arranged parallel with the image pick-up unit, and wherein:

the parallel portion includes a circular inner peripheral surface and a noncircular outer peripheral surface, and the noncircular outer peripheral surface includes, in a cross section thereof, orthogonal to the axial direction:

a facing side diameter reducing portion which is arranged on a side facing the image pick-up unit and which is closer to a central axis of the circular inner peripheral surface than an imaginary circular reference circumferential surface defined by the central axis of the circular inner peripheral surface at an outside of the circular inner peripheral surface; and a diameter keeping portion arranged on a side other than the side facing the image pick-up unit and whose at least a part overlaps the imaginary reference circumferential surface;

wherein the noncircular outer peripheral surface includes an opposite side diameter reducing portion in the cross section orthogonal to the axial direction which is arranged opposite to the facing side diameter reducing portion with respect to the central axis and which is closer to the central axis side than the imaginary reference circumferential surface.

2. The endoscope according to claim 1, wherein the channel tube is configured at least such that an accessory is to be inserted through the channel tube, the endoscope includes a bending portion operated to be bent in a bending direction, the distal end forming portion is provided on a distal end portion of the bending portion, and the diameter keeping portion is arranged on a bending directional side with respect to the central axis.

3. The endoscope according to claim 1, wherein the circular inner peripheral surface includes a circumferential surface, the facing side diameter reducing portion includes a plane surface, and the diameter keeping portion includes a circular arc peripheral surface wherein the whole diameter keeping portion overlaps the imaginary reference circumferential surface.

4. The endoscope according to claim 1, wherein the circular inner peripheral surface includes a circumferential surface, the noncircular outer peripheral surface includes an elliptic peripheral surface, the facing side diameter reducing portion is formed of a curved peripheral surface of the elliptic peripheral surface on an end portion side in a minor axial direction, and the diameter keeping portion is formed of a curved peripheral surface of the elliptic peripheral surface on an end portion side in a major axial direction and an end portion of the elliptic peripheral surface in the major axial direction overlaps the imaginary reference circumferential surface.

* * * * *